United States Patent
Imai et al.

(10) Patent No.: US 11,401,604 B2
(45) Date of Patent: Aug. 2, 2022

(54) FILM FORMATION METHOD

(71) Applicants: STRAWB Inc., Yokohama (JP); Kake Educational Institution, Okayama (JP); National University Corporation Okayama University, Okayama (JP)

(72) Inventors: Yuichi Imai, Yokohama (JP); Tatsuyuki Nakatani, Okayama (JP); Susumu Ozawa, Okayama (JP); Yasuhiro Fujii, Okayama (JP); Haruhito Uchida, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 235 days.

(21) Appl. No.: 16/491,684

(22) PCT Filed: Mar. 6, 2018

(86) PCT No.: PCT/JP2018/008442
§ 371 (c)(1),
(2) Date: Sep. 6, 2019

(87) PCT Pub. No.: WO2018/164083
PCT Pub. Date: Sep. 13, 2018

(65) Prior Publication Data
US 2020/0002809 A1    Jan. 2, 2020

(30) Foreign Application Priority Data
Mar. 6, 2017 (JP) .............................. JP2017-042037

(51) Int. Cl.
*C23C 16/27*    (2006.01)
*A61F 2/06*    (2013.01)
(Continued)

(52) U.S. Cl.
CPC .............. *C23C 16/272* (2013.01); *A61F 2/06* (2013.01); *A61L 27/303* (2013.01);
(Continued)

(58) Field of Classification Search
CPC ............ C23C 16/272; A61F 2/06; H05H 1/24
See application file for complete search history.

(56) References Cited

U.S. PATENT DOCUMENTS

| | | |
|---|---|---|
| 6,346,273 B1 | 2/2002 | Saettone et al. |
| 2011/0079582 A1 | 4/2011 | Yonesu et al. |

FOREIGN PATENT DOCUMENTS

| | | |
|---|---|---|
| JP | H05-237141 A | 9/1993 |
| JP | H06-246142 A | 9/1994 |

(Continued)

OTHER PUBLICATIONS

R1, Nanometer Scale Patterning and Processing, 2016, Purdue University, Lecture 46, Part 2 (Year: 2016).*

(Continued)

*Primary Examiner* — Dah-Wei D. Yuan
*Assistant Examiner* — Andrew J Bowman
(74) *Attorney, Agent, or Firm* — Alston & Bird LLP (57) ABSTRACT

A film formation method is provided with a step for disposing a non-electroconductive long thin tube 102 in a chamber 101 in which the internal pressure thereof is adjustable, generating a plasma inside the long thin tube 102 in a state in which a starting material gas including a hydrocarbon is supplied, and forming a diamond-like carbon film on an inner wall surface of the long thin tube 102. The long thin tube 102 is disposed in the chamber 101 in a state in which a discharge electrode 125 is disposed in one end part of the long thin tube 102 and the other end part is open. An alternating-current bias is intermittently applied between the
(Continued)

discharge electrode 125 and a counter electrode 126 provided so as to be separated from the long thin tube 102.

5 Claims, 4 Drawing Sheets

(51) Int. Cl.
  *A61L 27/30* (2006.01)
  *A61L 27/50* (2006.01)
  *A61L 27/56* (2006.01)
  *C23C 16/04* (2006.01)
(52) U.S. Cl.
  CPC ............. *A61L 27/507* (2013.01); *A61L 27/56*
          (2013.01); *C23C 16/045* (2013.01)

(56) References Cited

FOREIGN PATENT DOCUMENTS

| | | | | |
|---|---|---|---|---|
| JP | 2001-510810 | A | 8/2001 | |
| JP | 2006-216468 | A | 8/2006 | |
| JP | 2008-192567 | A | 8/2008 | |
| JP | 2008192567 | * | 8/2008 | ............... H05H 1/24 |
| JP | 2015-147974 | A | 8/2015 | |
| WO | WO-2009/123243 | A1 | 7/2011 | |

OTHER PUBLICATIONS

International Searching Authority, International Search Report and Written Opinion for International Application No. PCT/JP2018/008442, dated Jun. 5, 2018 (9 pages), Tokyo, Japan.

* cited by examiner

FIG. 7

FILM FORMATION METHOD

CROSS REFERENCE TO RELATED APPLICATIONS

This application is a national stage application, filed under 35 U.S.C. § 371, of International Application No. PCT/JP2018/008442, filed Mar. 6, 2018, which claims priority to Japan Application No. 2017-042037, filed Mar. 6, 2017, the contents of both of which as are hereby incorporated by reference in their entirety.

BACKGROUND

Technical Field

The present disclosure relates to a film formation method, and more particularly relates to a film formation method, a film formation apparatus, and a medical material for use to form a diamond-like carbon film on an inner wall surface of a long thin tube.

Description of Related Art

Medical materials that have recently grown in demand include an artificial blood vessel. Artificial blood vessels that have been typically used are made of polytetrafluoroethylene (ePTFE) containing polytetrafluoroethylene (PTFE) expanded to have its porosity increased. The ePTFE is a material having good biocompatibility, but is not sufficient to prevent occlusion. For this reason, the use of ePTFE artificial blood vessels with a diameter less than 6 mm is very risky.

Although a material derived from humans or animals may be used as a thin artificial blood vessel, such a material has problems in terms of safety and stable supply. To address these problems, there is a need for a thin artificial blood vessel not tissue-derived and difficult to occlude.

A diamond-like carbon (DLC) film, which is an amorphous carbon film containing $sp^2$ carbon, $sp^3$ carbon, and hydrogen, has superior biocompatibility. Thus, it is expected that forming a DLC film on an inner wall surface of an artificial blood vessel can make it difficult to occlude the artificial blood vessel. However, a DLC film is not easily formed on an inner wall surface of a long thin tube, such as an artificial blood vessel.

Examples of methods for forming a DLC film on an inner wall surface of a tube body include a method in which a discharge electrode is inserted into a tube body (see, for example, Patent Document 1). Further, consideration has been given also to a method in which a tube body is sandwiched between two electrode plates to generate plasma inside the tube body to form a film, without inserting the electrode into the tube body (see, for example, Patent Document 2).

Patent Document 1: Japanese Unexamined Patent Publication No. 2015-147974

Patent Document 2: Japanese Unexamined Patent Publication No. 2008-192567

BRIEF SUMMARY

However, the known film formation method has the following problems. If a discharge electrode is inserted into a tube body, the discharge electrode needs to be longer than the tube body on which a film is to be formed and to be thinner than the inside diameter of the tube body. The discharge electrode on which a high pressure is imposed needs to have a certain thickness or larger, thus making it actually impossible to form a film on an inner wall surface of a thin tube having a diameter of 6 mm or smaller. Further, shortening the distance between the discharge electrode and the inner wall surface may cause a metal component desorbed from the discharge electrode to adhere to the inner wall surface. If a carbon electrode is used as the discharge electrode, metal does not adhere to the inner wall surface. However, it is difficult to form a long thin carbon electrode.

If a tube body is sandwiched between two electrodes, large electrode plates are required to form a film over the entire long tube body. The tube body may be moved between the electrodes, or the electrodes may be moved along the tube body. However, in this case, a mechanism for moving the tube body is required. In addition, a hydrocarbon gas needs to be enclosed in the tube body. Thus, a film cannot be successfully formed on a porous artificial blood vessel even if the tube body is disposed directly between the electrodes.

It is expected that it is useful to form a DLC film on an inner wall surface of a catheter or any other similar object, because the formation of the DLC film provides advantages, such as high biocompatibility and a reduction in friction against the inner wall surface. However, a long thin tube for use in a catheter or any other similar object also causes a problem similar to that of an artificial blood vessel.

It is an object of the present disclosure to be able to easily form a DLC film on an inner wall surface of a medical material serving as a long thin tube.

A film formation method according to an aspect of the present disclosure includes: arranging a non-conductive long thin tube in a chamber capable of adjusting an internal pressure, and generating plasma inside the long thin tube while a source gas containing hydrocarbon is supplied into the chamber, and forming a diamond-like carbon film on an inner wall surface of the long thin tube. The long thin tube is disposed in the chamber such that a discharge electrode is disposed at one end of the long thin tube and such that the other end of the long thin tube is opened. An alternating current bias is intermittently applied between the discharge electrode and a counter electrode spaced apart from the long thin tube.

In the film formation method according to the aspect, the long thin tube may be porous, and may be disposed in the chamber while being housed in an outer cylinder having an inside diameter larger than an outside diameter of the long thin tube.

In this case, the long thin tube may be an artificial blood vessel.

In the film formation method according to the aspect, the long thin tube may be a catheter.

In one embodiment of the film deposition method, the counter electrode may be an inner wall surface of the chamber.

A film formation apparatus according to one aspect of the present disclosure includes: a chamber capable of adjusting an internal pressure; a gas feeder configured to feed a hydrocarbon gas into the chamber; a discharge electrode and a counter electrode provided in the chamber; and a power supply configured to intermittently apply an AC voltage between the discharge electrode and the counter electrode. The discharge electrode is attached to one end of a non-conductive long thin tube to discharge electricity with the counter electrode spaced apart from the long thin tube.

Plasma is thus generated in the long thin tube to form a diamond-like carbon film on an inner wall surface of the long thin tube.

The film formation apparatus according to the aspect may further include: an outer cylinder housing the long thin tube. The long thin tube may be porous.

A medical material according to one aspect of the present disclosure includes: a non-conductive long thin tube having an inside diameter from 0.1 mm to 6 mm and a length of 2 cm or more and having an inner wall surface on which a diamond-like carbon film is formed.

In the medical material according to the aspect, the long thin tube may be an artificial blood vessel or a catheter.

A film formation method of the present disclosure allows a DLC film to be easily formed on an inner wall surface of a medical material serving as a long thin tube.

DETAILED DESCRIPTION OF VARIOUS EMBODIMENTS

Figure 1:
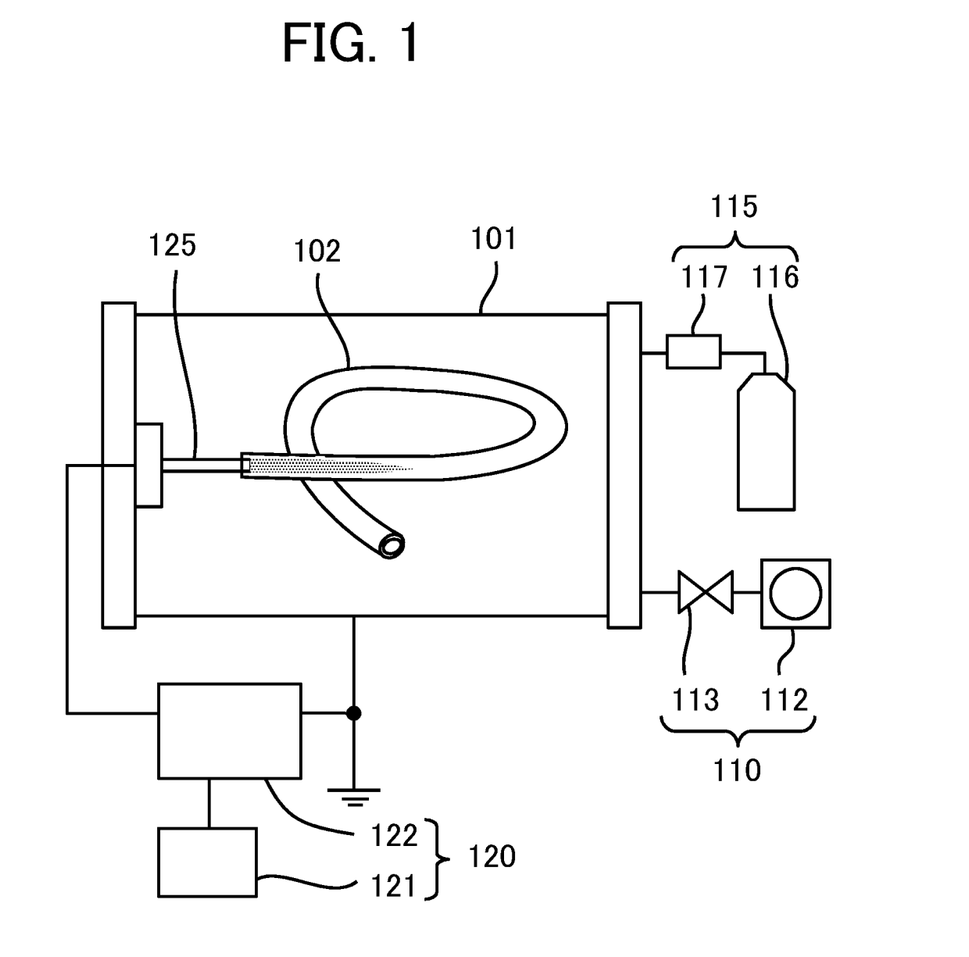
FIG. 1 is a schematic view showing a film formation apparatus according to an embodiment.

FIG. 1 shows a film formation apparatus for use in the present embodiment. The film formation apparatus includes a chamber 101 housing therein a long thin tube 102 on which a film is to be formed. The chamber 101 is connected to a vacuum evacuator 110 and a gas feeder 115 for feeding a film formation gas into the chamber 101. Thus, the internal pressure of the chamber 101 can be adjusted. A power supply 120 for supplying electric power is connected also to the chamber 101, in which plasma can be generated.

In the present embodiment, the vacuum evacuator 110 includes a vacuum pump 112 and a valve 113. In the present embodiment, the gas feeder 115 includes a cylinder 116 and a mass flow controller 117. The gas feeder 115 may also feed a plurality of gases. In the present embodiment, the power supply 120 includes a voltage generator 121 and an amplifier 122, and applies an alternating current (AC) voltage between the discharge electrode 125 and a counter electrode. The counter electrode is a ground electrode, and serves as an inner wall of the chamber 101.

One end portion of the long thin tube 102 disposed in the chamber 101 is disposed at the position of the discharge electrode 125, and the other end portion thereof is opened. After decompression of the inside of the chamber, a source gas containing hydrocarbon is supplied from a gas feeder 115, and an AC voltage is applied between the discharge electrode 125 and the inner wall of the chamber 101 serving as the counter electrode. The application of the AC voltage increases the ambient temperature of the discharge electrode 125. As a result, the internal pressure of the long thin tube 102 is slightly lower than the external pressure of the long thin tube 102, and plasma of hydrocarbon is generated in the vicinity of the discharge electrode 125. Since the other end of the long thin tube 102 is open, the generated plasma moves through the long thin tube 102 to the open end of the long thin tube 102, and plasma is generated across the long thin tube 102. As a result, a DLC film is formed on the inner wall surface of the long thin tube 102.

To sufficiently replace air in the chamber 101 with a source gas, the chamber is once decompressed to about $1\times10^{-3}$ Pa to $5\times10^{-3}$ Pa before the film formation. Examples of the hydrocarbon contained in the source gas include methane, ethane, propane, butane, ethylene, acetylene, and benzene, which are used in a usual CVD method. Methane is preferably used for ease of handling. The source gas may be a gas obtained by vaporizing an organic silicon compound, such as tetramethylsilane, or an oxygen-containing organosilicic compound, such as hexamethyldisiloxane. The source gas diluted with an inert gas, such as argon, neon, and helium, as necessary can be supplied. The source gas is preferably diluted with argon for ease of handling. If the source gas is diluted, the ratio of hydrocarbon to the inert gas is preferably about 10:1 to 10:5.

To uniformly form the DLC film in the long thin tube 102, the internal pressure of the chamber 101 is set to about 5 Pa to 200 Pa with the source gas supplied. Further, the flow rate of the source gas can be set to about 50 sccm to 200 sccm.

A bias voltage applied to the discharge electrode 125 to form a film can be set to about 1 kV to 20 kV. To avoid damage to the discharge electrode or a temperature rise, the bias voltage is preferably set to 10 kV or less. The frequency of the AC voltage is preferably set to about 1 kHz to 50 kHz. The AC voltage is preferably a pulse bias voltage intermittently applied, in view of reducing a rise in temperature. If an alternating current is a burst wave, the pulse repetition frequency is preferably set to about 3 pps to 50 pps. Depending on the inside diameter of the long thin tube 102, the film formation time, the applied AC voltage, and other factors, the pulse repetition frequency can be set to about 30 pps or less, so that the tube temperature is lower than or equal to 200° C. If the film formation rate is to be increased, the pulse repetition frequency needs to be increased. If the rise in temperature is to be reduced, the pulse repetition frequency needs to be decreased.

To stabilize electric discharge and form the DLC film to be adhesive, an offset negative voltage is preferably applied to the discharge electrode 125. The offset voltage may be about 0 kV to 3 kV.

The long thin tube 102 may be made of any non-conductive material. In the present disclosure, the term "non-conductive" means that a material has a resistivity of about $1\times10^8$ Ω/cm or more. Specifically, a fluororesin such as PTFE, a vinyl chloride resin, a polyurethane resin, a polyethylene resin, a polyolefin resin, a silicone resin, or any other resin can be used. Specific applications for long thin tubes should not be specifically limited, but include a medical material for use in a medical instrument that contacts blood, such as a catheter and an artificial blood vessel.

The inside diameter of the long thin tube 102 should not be specifically limited. However, if the long thin tube 102 is an artificial blood vessel, a catheter, or any similar object, the inside diameter of the long thin tube 102 is preferably 10 mm or less, more preferably 6 mm or less, still more preferably 4 mm or less, and preferably 0.1 mm or more, more preferably 0.2 mm or more. The length of the long thin tube 102 should not be specifically limited. However, if the long thin tube 102 is an artificial blood vessel, a catheter, or any similar object, the length of the long thin tube 102 is preferably 2 cm or more, more preferably 4 cm or more, and still more preferably 10 cm or more. To uniformly form a film, the length of the long thin tube 102 is preferably 5 m or less, more preferably 3 m or less, and still more preferably 1.5 m or less. However, adjusting the film formation conditions allows a film to be formed on the inner wall of the thin tube having a length of 5 m or more.

Figure 2:
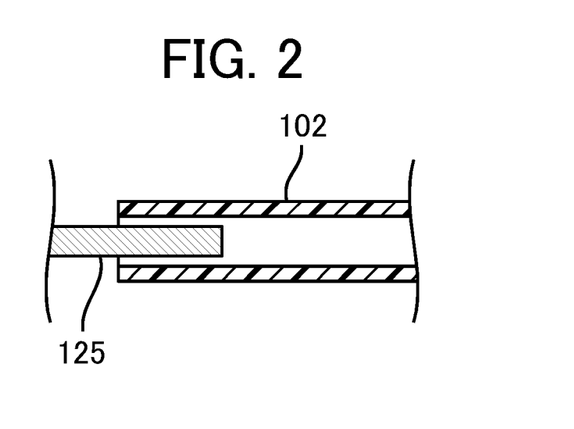
FIG. 2 is a cross-sectional view showing a connection portion of a discharge electrode.
Figure 3:
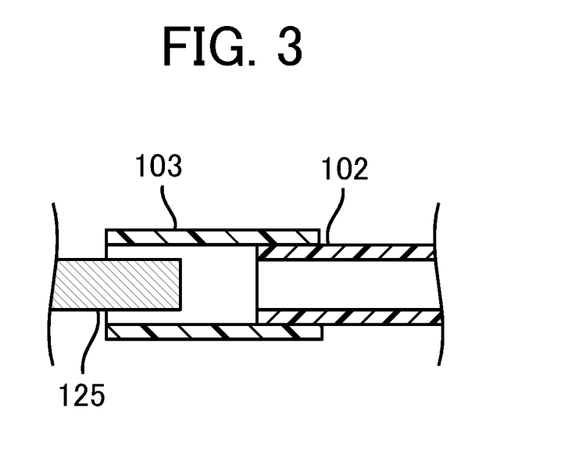
FIG. 3 is a cross-sectional view showing a variation of the connection portion of the discharge electrode.

The discharge electrode 125 merely needs to be disposed at one end of the long thin tube 102. In the present embodiment, a state where the discharge electrode 125 is disposed at an end of the long thin tube 102 may correspond to any one of the following states. First, as shown in FIG. 2, at least the tip of the discharge electrode 125 may be located inside the long thin tube 102. Alternatively, as shown in FIG. 3, an electrode connector 103 may be connected to an end portion of the long thin tube 102, and at least the tip of the discharge electrode 125 may be located inside the electrode connector 103. The electrode connector 103 may be configured as an insulating tube or any suitable object. In FIG. 3, the electrode connector 103 is a tube to be fitted onto the long thin tube 102, but may be a tube to be fitted into the long thin tube 102. Alternatively, a plurality of tubes may be combined together to form the electrode connector 103. In this case, a hard material may be used for a portion, of the electrode connector 103, connecting to the long thin tube 102, and a flexible material may be used for the other portion, of the electrode connector 103, connecting to the long thin tube 102. Such a configuration makes handling of the electrode connector easy.

Figure 4:
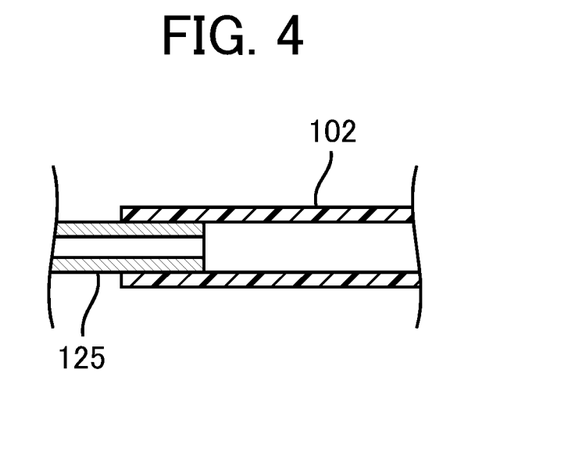
FIG. 4 is a cross-sectional view showing a variation of the discharge electrode.

The discharge electrode 125 may have an outside diameter smaller than the inside diameter of the long thin tube 102 or the electrode connector 103, so that a source gas is supplied into the long thin tube 102 through an end of the long thin tube 102 near the discharge electrode 125. Alternatively, as shown in FIG. 4, the discharge electrode 125 may be hollowed such that the source gas is supplied into the long thin tube 102.

The discharge electrode 125 merely needs to be electrically conductive, and may be, for example, a metal. If the discharge electrode 125 is made of a metal, stainless steel is preferable to increase the corrosion resistance, for example. Inserting the metal electrode through the thin tube may cause the metal to be transferred from the electrode to the thin tube. However, in the case of the film formation apparatus of the present embodiment, using the electrode connector 103 almost prevents the metal from affecting the thin tube. Even if no electrode connector 103 is used, the metal hardly affects a portion of the thin tube that is about 5 cm or more away from the discharge electrode 125. To prevent the metal from affecting the thin tube, the discharge electrode 125 is preferably a carbon electrode. In the case of the film formation apparatus of the present embodiment, the carbon electrode can also be easily formed.

Figure 5:
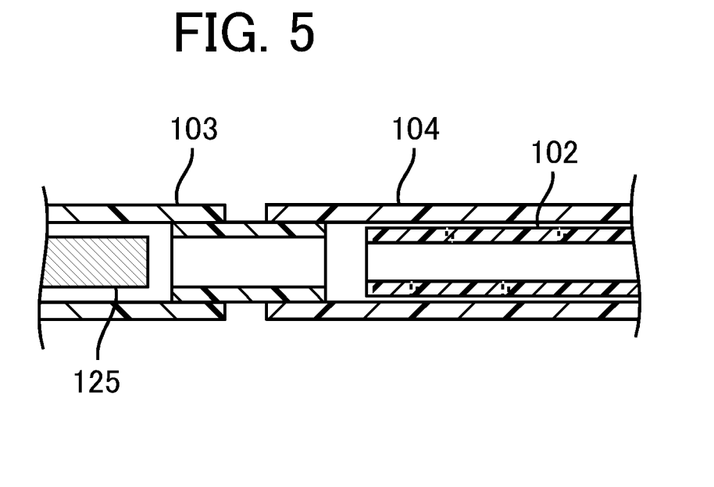
FIG. 5 is a cross-sectional view showing a variation in which an outer cylinder is used.

If the long thin tube 102 is porous, and no pressure difference is created between the inside and outside of the long thin tube 102, plasma cannot be generated in the long thin tube 102. In this case, as shown in FIG. 5, the long thin tube 102 is housed in an outer cylinder 104, and a pressure difference is thus created between the inside and outside of the outer cylinder 104, thereby forming a film.

Just like the long thin tube 102, the outer cylinder 104 is non-conductive to generate plasma inside the outer cylinder 104. Specifically, plastic or any other material is used. The outer cylinder 104 may be formed of a flexible, soft material, or may be formed of a hard material. Making the outer cylinder 104 transparent or semi-transparent allows the plasma generated to be visually identified.

The outer cylinder 104 to be used has a wall surface with no pores, for example, so that a pressure difference is created between the inside and outside of the outer cylinder 104 due to a temperature rise caused when an AC voltage is applied to the discharge electrode 125. The outer cylinder 104 merely needs to have an inside diameter larger than the outside diameter of the long thin tube 102, and a length longer than or equal to a length that allows the entire long thin tube 102 to be housed therein. An end of the outer cylinder 104 remote from the long thin tube 102 is open.

If the inside diameter of the outer cylinder 104 is made substantially equal to the outer shape of the long thin tube 102, and substantially no gap is formed between the outer wall surface of the long thin tube 102 and the inner wall surface of the outer cylinder 104, plasma may be substantially present only inside the long thin tube 102, and a film may be formed only on the inner wall surface of the long thin tube 102. Enlarging the gap between the outer wall surface of the long thin tube 102 and the inner wall surface of the outer cylinder 104 may cause plasma to be present also outside the long thin tube 102, and a film may be formed not only on the inner wall surface of the long thin tube 102 but also on the outer wall surface thereof.

FIG. 5 shows an example in which the discharge electrode 125 is disposed at an end of the long thin tube 102 by using the electrode connector 103 fitted into the outer cylinder 104. However, the electrode connector 103 may be fitted onto the outer cylinder 104. Alternatively, the tip of the discharge electrode 125 may be located inside the outer cylinder 104 without using the electrode connector 103. In this case, the tip of the discharge electrode 125 may be located inside the long thin tube 102.

Even if the long thin tube 102 is a catheter or any other similar object, and is not porous, a film may be formed while the long thin tube 102 is housed in the outer cylinder 104.

Figure 6:
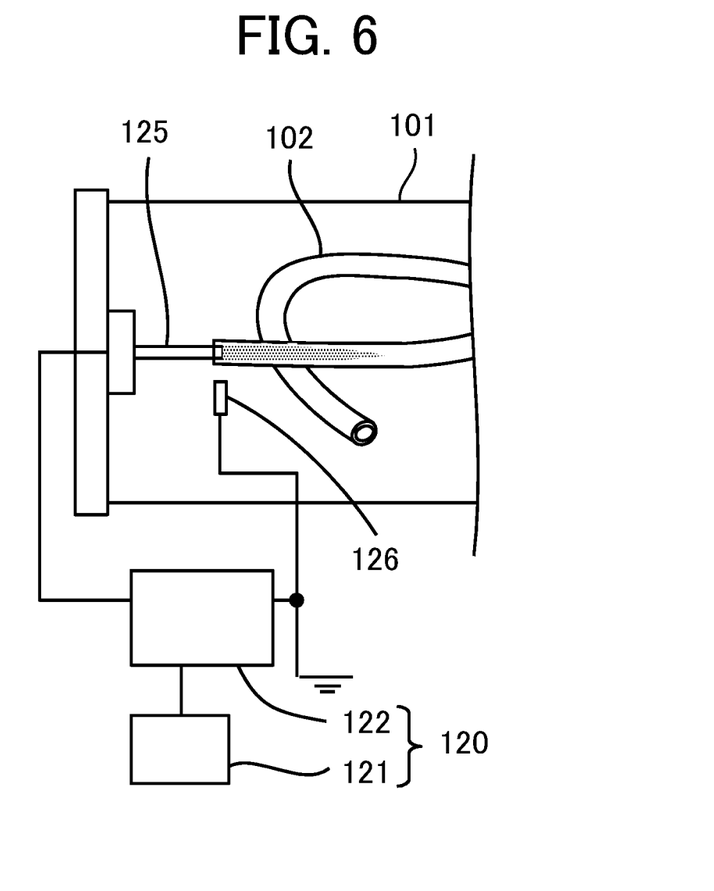
FIG. 6 is a cross-sectional view showing a variation of a counter electrode.

In the present embodiment, the counter electrode is the inner wall of the chamber 101. However, as shown in FIG. 6, a counter electrode 126 may face the discharge electrode 125 with the long thin tube 102 interposed therebetween. Arranging the counter electrode 126 as described above allows plasma to be stably generated even if the AC voltage is lowered. This arrangement is merely an example of the present disclosure. The counter electrode 126 may be provided at any position within the chamber. Even if the counter electrode 126 is in contact with the long thin tube 102, plasma can be generated. However, if the counter electrode 126 is made of a metal, spacing the counter electrode 126 apart from the long thin tube 102 can make it difficult to contaminate the long thin tube 102 with metal.

The thickness of the DLC film formed on the inner wall of the long thin tube 102 should not be specifically limited, but is preferably 3 nm or more, more preferably 10 nm or more, to keep the artificial blood vessel from occlusion and to reduce the coefficient of friction of the inner surface of the catheter. Further, to prevent the DLC film from peeling off, the thickness of the DLC film is preferably 50 nm or less, more preferably 30 nm or less.

The film formation time needs to be long enough to allow the DLC film to have a necessary thickness, and needs to be appropriately selected in accordance with the film formation conditions, such as the inside diameter of the long thin tube, the AC voltage, and the pulse repetition frequency. To improve the productivity, the film formation time is preferably 60 minutes or shorter, more preferably 30 minutes or shorter, still more preferably 10 minutes or shorter.

EXAMPLES

<Film Formation Apparatus>

A DLC film was formed on an inner wall surface of a specimen by the film formation apparatus shown in FIG. 1. A chamber 101 was a stainless steel container having a diameter of 200 mm and a length of 500 mm. The chamber 101 was connected to a vacuum evacuator 110 and a gas feeder 115. A power supply 120 includes a voltage generator 121 (SG-4104 manufactured by IWATSU ELECTRIC CO., LTD) and an amplifier 122 (HVA 4321 manufactured by NF Corporation). A discharge electrode 125 was a stainless steel electrode having a diameter of 6 mm and a length of 70 mm. The gas feeder 115 is configured to feed a source gas from a cylinder 116 containing methane gas through a mass flow controller 117. The internal pressure of the chamber 110 was adjusted through control of the opening degree of a valve and the amount of gas fed.

<Evaluation of DLC Film>

Whether or not a film was formed was checked using a Raman spectrometer (RAMAN-11 manufactured by Nanophoton Corporation). The measurement conditions included a light source wavelength of 532 nm, an objective lens magnification of 50×, a numerical aperture of 0.8, and a diffraction grating of 600 gr/mm.

<Film Formation on Silicon Tube>

A DLC film was formed on the inner wall of each of nine types of silicon tubes having an inside diameter of any one of 2 mm, 3 mm, and 4 mm, and a length of any one of 500 mm, 1000 mm, and 1500 mm. The source gas was $CH^4$, the flow rate of the source gas was 96.2 ccm (at room temperature), and the internal pressure of the chamber was 39.06 Pa. The bias voltage during the film formation was set to 5 kV, and its frequency was set to 10 kHz. An AC voltage was intermittently applied to the discharge electrode 125 for five minutes such that the pulse repetition frequency was 10 pps or 30 pps. During the film formation, an offset of 2 kV was applied to the discharge electrode 125 by the amplifier.

In any of the specimens, plasma was generated in a tube from an end of the tube near an electrode to an open end of the tube, and a DLC film was thus formed on the inner wall surface of the tube.

During the film formation, a temperature sensitive label (manufactured by Palmer Wahl Instruments, Inc.) was placed at a position 5 cm away from the electrode, and then the internal temperature of the tube was measured. When the pulse repetition frequency was 10 pps, the internal temperature was 132° C. to 154° C. When the pulse repetition frequency was 30 pps, the internal temperature was 171° C. to 193° C.

<Film Formation on Artificial Blood Vessel>

An ePTFE artificial blood vessel having an inside diameter of 4 mm, an outside diameter of 5 mm, and a length of 150 mm (SGTW-0415BT manufactured by W.L. Gore & Associates, Co., LTD.) was placed in an outer cylinder having an inside diameter of 5 mm and a length of 150 mm and configured as a silicon tube. In this state, a film was formed. The film formation conditions were the same as those on which the film was formed on the silicon tube. The film formation time was 5 minutes, 20 minutes, and 40 minutes.

Figure 7:
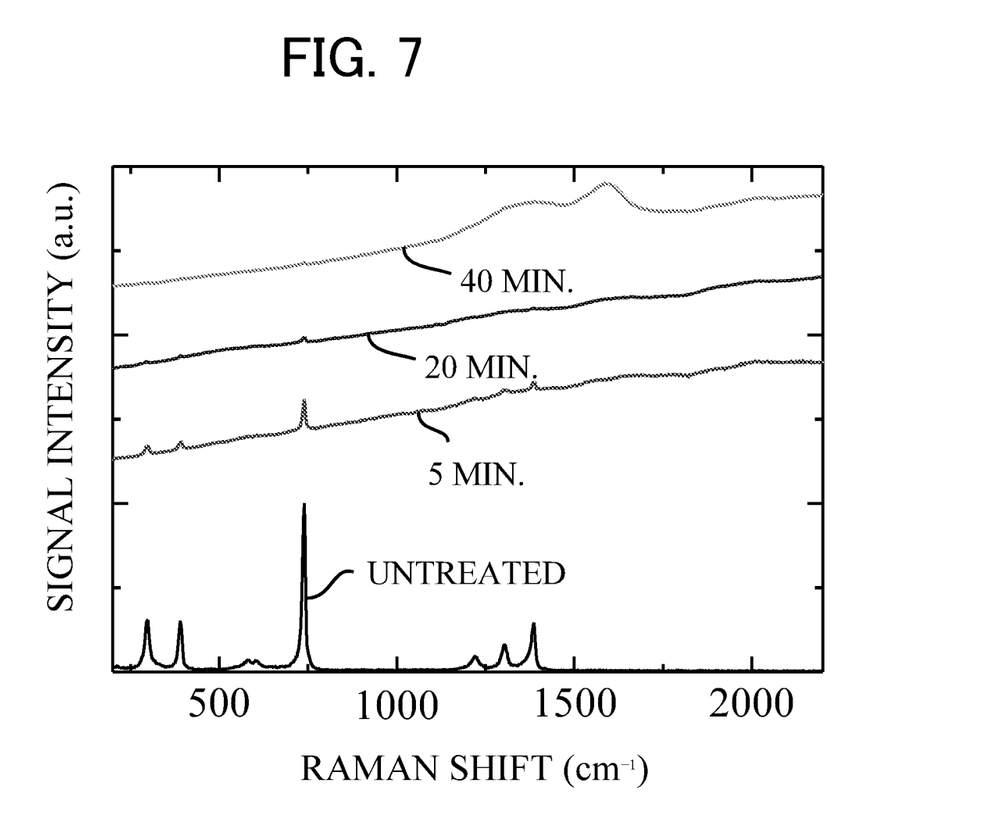
FIG. 7 is a Raman spectrum of a specimen.

Plasma was generated in the artificial blood vessel, and a DLC film was thus formed. FIG. 7 shows exemplary Raman spectrum measurements. As the film formation time increases, a spectral peak specific to PTFE becomes weaker. The D-band of carbon has a peak around 1330 $cm^{-1}$, and the G-band of carbon has a peak around 1550 $cm^{-1}$.

A portion of a specimen located near the open end of the specimen and having a length of 100 mm is cut into 20-mm-long test pieces. The film adhesion of each of the test pieces was evaluated. Each test piece was formed into a dumbbell shape having a reduced section and grip sections. The width of the reduced section was 3 mm, the length of the test piece was 10 mm, and the width of each of the grip sections was 10 mm. The test pieces underwent tensile testing using a tensile tester (Force Gauge MX-500N, manufactured by IMADA CO., LTD.) such that their distortion factors were 20%, 40%, 60%, and 80%, respectively. Whether or not the film of each of the test pieces having the distortion factors described above peeled off was checked. Although each test piece underwent tensile testing until its distortion factor reached 80%, no peeled DLC film was observed.

The film formation method of the present disclosure allows a DLC film to be easily formed on an inner wall surface of a long thin tube, and is useful as, for example, a method for manufacturing a medical material.

DESCRIPTION OF REFERENCE CHARACTERS

101 Chamber
102 Long Thin Tube
103 Electrode Connector
104 Outer Cylinder
110 Vacuum Evacuator
112 Vacuum Pump
113 Valve
115 Gas Feeder
116 Cylinder
117 Mass Flow Controller
120 Power Supply
121 Voltage Generator
122 Amplifier
125 Discharge Electrode
126 Counter Electrode

The invention claimed is:

1. A film formation method comprising:
   arranging a non-conductive tube in a chamber capable of adjusting internal pressure:
   generating plasma inside the tube while a source gas containing hydrocarbon is supplied into the chamber; and
   forming a diamond-like carbon film on an inner wall surface of the tube, the tube being disposed in the chamber, directly or while being housed in an outer cylinder having an inside diameter larger than an outside diameter of the tube, such that a discharge electrode is disposed near a first end of the tube, and such that a second and opposing end of the tube is opened,
   inserting the discharge electrode either: into the first end of the tube or of the outer cylinder, or into an electrode connector cylinder connected to the first end of the tube or of the outer cylinder, and
   intermittently applying an alternating current bias between the discharge electrode and a counter electrode spaced apart from the tube.

2. The film formation method of claim 1, wherein the tube is porous, and is disposed in the chamber while being housed in the outer cylinder.

3. The film formation method of claim 2, wherein the tube is an artificial blood vessel.

4. The film formation method of claim 1, wherein the tube is a catheter.

5. The film formation method of claim 1, wherein the counter electrode is an inner wall surface of the chamber.

\* \* \* \* \*

UNITED STATES PATENT AND TRADEMARK OFFICE
CERTIFICATE OF CORRECTION

PATENT NO. : 11,401,604 B2
APPLICATION NO. : 16/491684
DATED : August 2, 2022
INVENTOR(S) : Yuichi Imai et al.

It is certified that error appears in the above-identified patent and that said Letters Patent is hereby corrected as shown below:

On the Title Page

Item (73) Assignee:
"NATIONAL UNIVERSITY CORPORATION OKAYAMA UNIVERSITY, Okayama (JP)"
Should read:
--STRAWB INC., Yokohama (JP); KAKE EDUCATIONAL INSTITUTION, Okayama (JP); NATIONAL UNIVERSITY CORPORATION OKAYAMA UNIVERSITY, Okayama (JP)--

Signed and Sealed this
Tenth Day of January, 2023

Katherine Kelly Vidal
*Director of the United States Patent and Trademark Office*